(12) United States Patent
Vachon

(10) Patent No.: US 7,153,265 B2
(45) Date of Patent: Dec. 26, 2006

(54) ANTI-INFLAMMATORY BIOSENSOR FOR REDUCED BIOFOULING AND ENHANCED SENSOR PERFORMANCE

(75) Inventor: David J. Vachon, Granada Hills, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 584 days.

(21) Appl. No.: 10/127,745

(22) Filed: Apr. 22, 2002

(65) Prior Publication Data

US 2003/0199837 A1    Oct. 23, 2003

(51) Int. Cl.
A61B 5/05 (2006.01)
A61B 5/00 (2006.01)

(52) U.S. Cl. .............. 600/365; 600/345; 600/347

(58) Field of Classification Search ........... 600/345, 600/347, 353, 354, 365, 366, 372, 373, 377, 600/300, 309, 310, 316, 395–397, 362
See application file for complete search history.

(56) References Cited

U.S. PATENT DOCUMENTS

| | | | |
|---|---|---|---|
| 4,557,724 A | | 12/1985 | Gregonis et al. |
| 4,559,033 A | | 12/1985 | Stephen et al. |
| 4,671,288 A | | 6/1987 | Gough |
| 4,723,947 A | | 2/1988 | Konopka |
| 5,265,608 A | * | 11/1993 | Lee et al. ............... 600/377 |
| 5,284,140 A | * | 2/1994 | Allen et al. ............ 600/373 |
| 5,320,725 A | | 6/1994 | Gregg et al. |
| 5,403,700 A | | 4/1995 | Heller et al. |
| 5,411,527 A | * | 5/1995 | Alt ........................ 607/5 |
| 5,540,828 A | | 7/1996 | Yacynych |
| 5,749,832 A | | 5/1998 | Vadgama et al. |
| 5,777,060 A | | 7/1998 | Van Antwerp |
| 5,786,439 A | | 7/1998 | Van Antwerp et al. |
| 5,925,552 A | * | 7/1999 | Keogh et al. ............ 435/174 |
| 5,965,380 A | | 10/1999 | Heller et al. |
| 6,119,028 A | | 9/2000 | Schulman et al. |
| 6,134,461 A | * | 10/2000 | Say et al. ............. 600/345 |
| 6,212,416 B1 | * | 4/2001 | Ward et al. ............ 600/345 |
| 6,256,522 B1 | | 7/2001 | Schultz |
| 6,295,474 B1 | | 9/2001 | Munshi |

OTHER PUBLICATIONS

"Hydromer® product description," obtained from www.hydromer.com on Dec. 21, 2001.

* cited by examiner

*Primary Examiner*—Charles A Marmor, II
*Assistant Examiner*—Navin Natnithithadha
(74) *Attorney, Agent, or Firm*—Gates & Cooper LLP

(57) ABSTRACT

A biosensor including an external surface, and an accessory material in close proximity to the external surface. The accessory material includes a coating containing a hydrophilic material and/or a fiber modified to deliver a therapeutic agent. The biosensor modifies a biological response to the biosensor upon contact with a tissue, such as upon implantation into the skin of a subject, thereby reducing biofouling, inflammation and other undesirable tissue responses that interfere with biosensor performance. The biosensor can be any biocompatible sensor, suitable for short- or long-term use. Preferably, the biosensor is an enzymatic or electrochemical sensor, such as a glucose sensor. Also provided are a method of producing a biosensor and a method of delivering a biologically active substance to a subject.

26 Claims, 3 Drawing Sheets

ANTI-INFLAMMATORY BIOSENSOR FOR REDUCED BIOFOULING AND ENHANCED SENSOR PERFORMANCE

TECHNICAL FIELD OF THE INVENTION

This invention relates generally to the manufacture and use of a biosensor suitable for subcutaneous implantation. The biosensor is capable of minimizing protein biofouling and inflammatory reactions that degrade sensor performance.

BACKGROUND OF THE INVENTION

Biomedical sensors, such as enzyme electrodes, can be used to determine the concentration of certain biochemicals rapidly and with considerable accuracy. Enzyme electrodes can detect glucose, urea, uric acid, various alcohols, and a number of amino acids under certain well-defined conditions. For example, glucose sensors suitable for in vivo use can be prepared by depositing a glucose sensitive enzyme, such as glucose oxidase, onto an electrode via an electromotive plating process.

Sensor configurations currently in use require a minimum of one polymeric membrane at the interface with the in vivo environment. This membrane (external surface) serves two functions. First, the membrane limits diffusion, e.g. of glucose, while maintaining high oxygen permeability. Second, the membrane provides a biocompatible interface with the surrounding tissue.

The introduction of a material into the body, however, initiates protein fouling or deposition at the surface of the material or device. Following the deposition of protein at the surface, a new surface is essentially created. This new surface influences the temporal sequence of events associated with the healing process. In the context of a biosensor, shortly after the injury initiated by implantation of the sensor, monocytes arrive at the material surface and differentiate into macrophages soon thereafter.

Macrophages are potent generators of damaging chemicals that aid in the process of phagocytosis. These chemical entities and by-products can include hydroxyl radical, superoxide, and strong acids, which may diffuse through the membrane to the underlying enzyme layer.

SUMMARY OF THE INVENTION

To overcome the limitations in the prior art described above, and to overcome other limitations that will become apparent upon reading and understanding the present specification, embodiments of the invention provide a biosensor including a sensor having an external surface, and an accessory material adhered, affixed, or otherwise provided in close proximity to the external surface, where the accessory material modifies the biological response of a tissue that is in contact with the biosensor. Representative biological responses include protein deposition, inflammation and proliferation of macrophages and/or foreign body giant cells.

In one embodiment, the accessory material comprises a coating containing a hydrophilic polymer. Examples of hydrophilic polymers include, but are not limited to, polyhydroxyethylmethacrylate (PHEMA), polysaccharide, polyacrylamide, polyurea, polyethylene oxide (PEO) containing polyurethane, PEO containing polyurea and cross-linked PEO. In a preferred embodiment, the coating further includes an anti-inflammatory agent, such as dexamethasone or a salt thereof. Suitable water-soluble salts include, but are not limited to, sodium phosphate or acetate forms or derivatives. In another embodiment, the accessory material comprises a fiber. Preferably, the fiber is modified to deliver a therapeutic agent. Exemplary fiber materials include, but are not limited to, polypropylene, polyurethane, polyester, degradable suture materials (e.g., PLA, PGA, PLGA).

In some embodiments, the external surface of the biosensor includes a hydrophobic polymeric membrane. The biosensor can be any biocompatible sensor, suitable for short or long-term use. In preferred embodiments, the biosensor is an optical, optochemical, molecular recognition, enzymatic or electrochemical sensor. One example of a biosensor includes a glucose sensor.

The invention additionally provides a method of producing a biosensor having an accessory material affixed thereto. In one embodiment, the method includes coating a sensor with a hydrophilic material, such as a material containing a polyethylene oxide (PEO) component. Preferably, the PEO is sprayed, painted, dipped or spun onto the sensor. In another embodiment, the method includes affixing a fiber to the external surface of a biosensor or otherwise providing a fiber in close proximity to the external surface of the sensor. Preferably, the fiber or hydrophilic material is modified to deliver an anti-inflammatory or other therapeutic agent. The invention additionally provides a method for delivering a biologically active substance to a subject using a biosensor of the invention.

DETAILED DESCRIPTION

All scientific and technical terms used in this application have meanings commonly used in the art unless otherwise specified. As used in this application, the following words or phrases have the meanings specified.

As used herein, "modifying the biological response of a tissue" means altering a biological response that occurs in tissue upon introduction of a foreign object, such as an implanted biosensor. Examples of such biological responses include protein biofouling or deposition, inflammation, macrophage and/or foreign body giant cell invasion and/or proliferation. Typically, the modifying includes inhibiting or minimizing undesirable biological responses that reduce or impede biosensor performance.

As used herein, "hydrophilic polymer" means a polymer having a strong tendency to bind or absorb water, which is sufficient to result in swelling and formation of gels. This property is characteristic of some natural polymers, including carbohydrates, proteins and man-made polymers (e.g., hydrogels).

As used herein, "affixed to" means attached to, stuck to or fused with such that a substance affixed to a surface remains substantially attached to or closely associated with the surface.

As used herein, "provided in proximity to" means that a substance or material is affixed to or positioned alongside another substance or material sufficiently close so that molecules released by one substance or material will influence the chemical and biological environment of the other substance or material. Typically, in the context of a fiber serving as an accessory material to a sensor, the fiber can be provided in proximity to the sensor by co-implantation of the fiber and the sensor, whereby the two materials may or may not be in physical contact along some or all of their lengths, yet molecules released by the fiber will influence the biological response of the tissue into which the sensor has been implanted.

As used herein, "a" or "an" means at least one, and unless clearly indicated otherwise, includes a plurality.

Overview

Embodiments of the invention provide a biosensor including a sensor having an external surface, and an accessory material affixed to the external surface. In one embodiment the accessory material includes a coating containing a hydrophilic material, such as a hydrophilic polymer. In another embodiment, the accessory material includes a fiber. In a preferred embodiment, the accessory material is modified to deliver a therapeutic agent. The accessory material of the biosensor embodiment of the invention provides for improved biocompatibility by reducing biofouling and other undesirable effects of the biological response to an implanted device, and also provides enhanced sensor performance. Further enhancement of sensor performance can be provided by including an anti-inflammatory agent in the accessory material.

Biosensor

Figure 1:
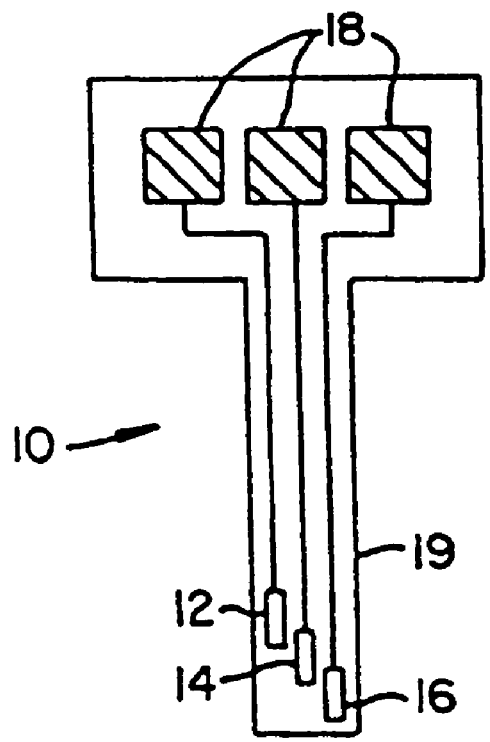
FIG. 1A is a schematic top view of a sensor 10 comprising an electrode 14 in accordance with the present invention.
FIG. 1B is a sectional side view of a working electrode 14 prepared in accordance with the present invention.
Figure 1:
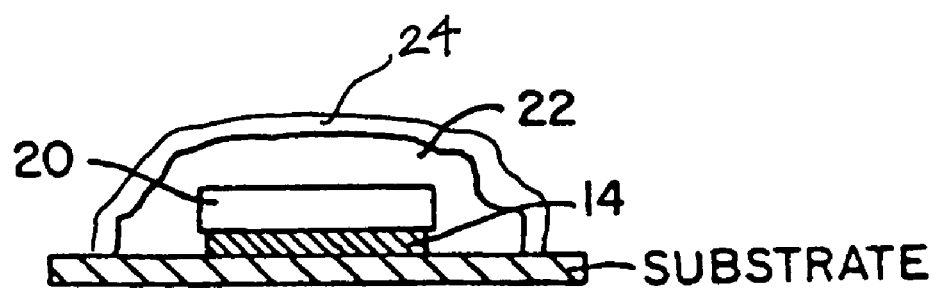

FIG. 1 illustrates an exemplary sensor 10 including a working electrode 14 plated with an enzyme. As shown in FIG. 1A, a sensor 10 can have a reference electrode 12, a working electrode 14, and a counter electrode 16 deposited on a polymeric sheet 19. The sensor 10 further includes a series of bonding pads 18. FIG. 1B shows a cross-sectional view of the working electrode 14 covered with a layer 20 of an enzyme, such as glucose oxidase. The entire electrode array can then be coated with a layer 22 of a polymer. The electrodes can be made of any conductive surface, e.g., gold, platinum, palladium, chromium, copper, aluminum, pyrolitic carbon, composite material (e.g., metal-polymer blend), nickel, zinc, titanium, or an alloy, such as cobalt-nickel-chromium, or titanium-aluminum-vanadium, which is deposited on any of a variety of suitable materials, including glass, polyimide or polyester. In some embodiments, the electrode array includes a flex-circuit layout/design. Of course, those skilled in the art will recognize that variations of the above components, and other types of electrodes can be used in the method of the invention. The sensor 10 is coated further with a hydrophilic polymer 24, which provides for reduction of biofouling and enhanced sensor performance in a biological environment.

Figure 2A:
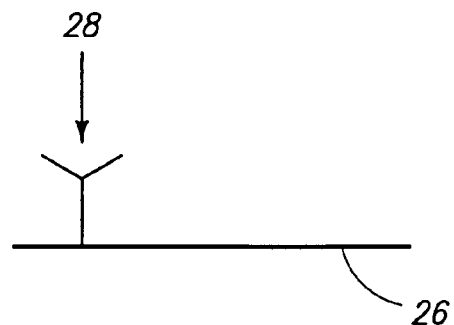
FIG. 2A is a schematic side view of an optical affinity sensor 26 without a coating, showing a representative glucose binding site 28.
Figure 2B:
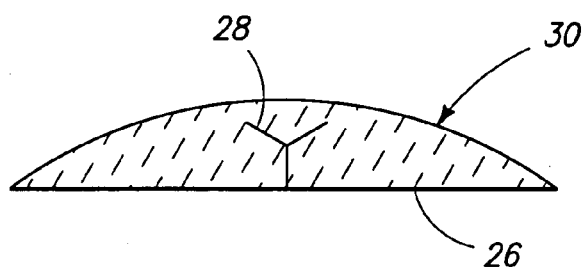
FIG. 2B is a schematic side view of an optical sensor 26 as shown in FIG. 2A, but with a coating 30.

In some embodiments, the biosensor is an optical affinity sensor. FIG. 2A is a schematic side view of an optical affinity sensor 26 without a coating, showing a representative glucose binding site 28. The sensor 26, which includes a reflective substrate, can be coated with a hydrophilic, biocompatible and glucose permeable coating 26, as shown schematically in FIG. 2B. Optical sensors for detection of analytes are described in U.S. Pat. Nos. 6,256,522, and 5,143,066.

Other examples of sensors are described in U.S. Pat. No. 4,671,288 (electrochemical sensor); U.S. Pat. No. 5,320,725 (amperometric sensor); U.S. Pat. No. 5,403,700 (polyimide-based sensor design); and U.S. Pat. No. 5,540,828 (sensor with a polymer-modified surface). Those skilled in the art can readily appreciate the ability to adapt the teachings of the present invention to a variety of known sensor types and configurations.

Hydrophilic Coating

In some embodiments, the accessory material includes a hydrophilic coating. The coating applied to a biosensor embodiment of the invention includes a hydrophilic polymer. Examples of hydrophilic materials include, but are not limited to, polyureas, polyamides, polyurethanes, acrylates, polyesters, polyethylene oxide (PEO) or cross-linked PEO. A preferred hydrophilic material for use in accordance with the invention is a PEO containing polyurethane or PEO containing polyurea. PEOs can be cross-linked by a variety of methods known in the art, including via the use of a gas plasma, or ionizing radiation such as electron or gamma sources, for example.

It is desirable to obtain a very hydrophilic membrane at the interface between the sensor and the biological environment. Accordingly, the coating is at least sufficiently hydrophilic to achieve swelling and gel formation. Preferably, the coating is sufficiently hydrophilic that, upon contact with a wet environment, it achieves a swell volume of at least about two, three, four or five times the thickness of the coating in a dry environment. Preferably, the coating is sufficiently hydrophilic, oxygen permeable and/or optically transparent so as to not change the overall analyte sensing capability of the sensor. Ideally, the coating achieves the maximal swell volume that does not disrupt adhesion with the underlying material.

Preferred hydrophilic materials include, but are not limited to, PEO containing polyurethanes, such as HydroMed™ TPH-D640 (available from CardioTech International). Such a polyurethane is suitable for application over the top of polymeric coatings currently in use with glucose sensors, such as glucose limiting polymer (GLP; MiniMed, Inc., Northridge, Calif.). In such applications, the hydrophilic material preferably does not limit glucose and is readily incorporated into the sensor production process.

Preferably the hydrophilic material is applied by spraying the coating onto the sensor surface, e.g., over the GLP or optochemical sensing polymer. The preferred polymer does not impede the diffusion of glucose, is soluble in a volatile organic solvent, such as tetrahydrofuran (THF) or isopropyl alcohol or mixture thereof (e.g., 25/75), that is suitable for spraying without disrupting the original surface. Damage to the underlying surface could affect the mass transfer properties of the underlying material and result in erratic sensor behavior. Alternatively, the hydrophilic material can be applied by painting or other means known in the art.

Fiber

In another embodiment, the accessory material comprises a fiber. Representative fiber materials include, but are not limited to, natural fibers such as cotton, polypropylene, polyurethane, polyester, degradable suture materials such as polylactic acid (PLA) and polyglycolic acid (PGA) and co-polymers of lactic acid and glycolic acid (PLGA), or other materials that can be formulated with a therapeutic agent. The fiber is preferably modified to deliver a therapeutic agent. The therapeutic agent can be integrated into the fiber during fiber production, or applied to an existing fiber as a coating.

Figure 3A:
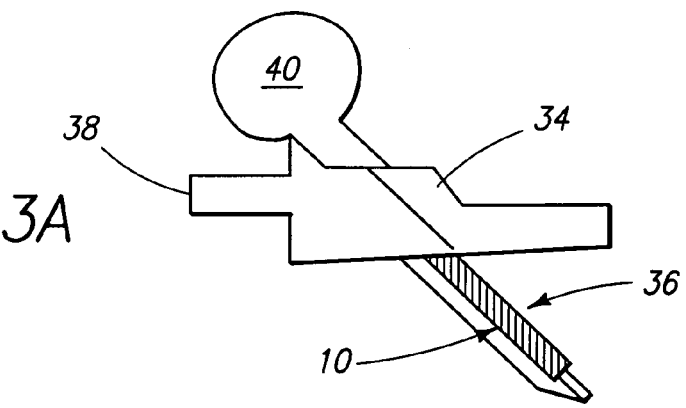
FIG. 3A is a schematic side view of a sensor 10 and fiber 32 inserted through the skin with the assistance of a connector 38 and a needle 36 that houses the sensor and fiber.
Figure 3B:
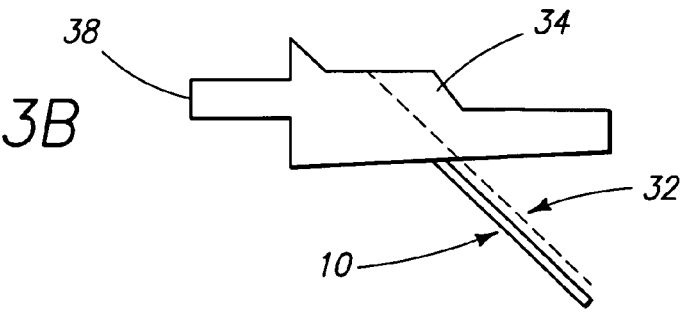
FIG. 3B is a schematic side view of the sensor 10 shown in FIG. 3A after removal of the needle 36, leaving the sensor 10 and fiber 32 in place.
Figure 4:
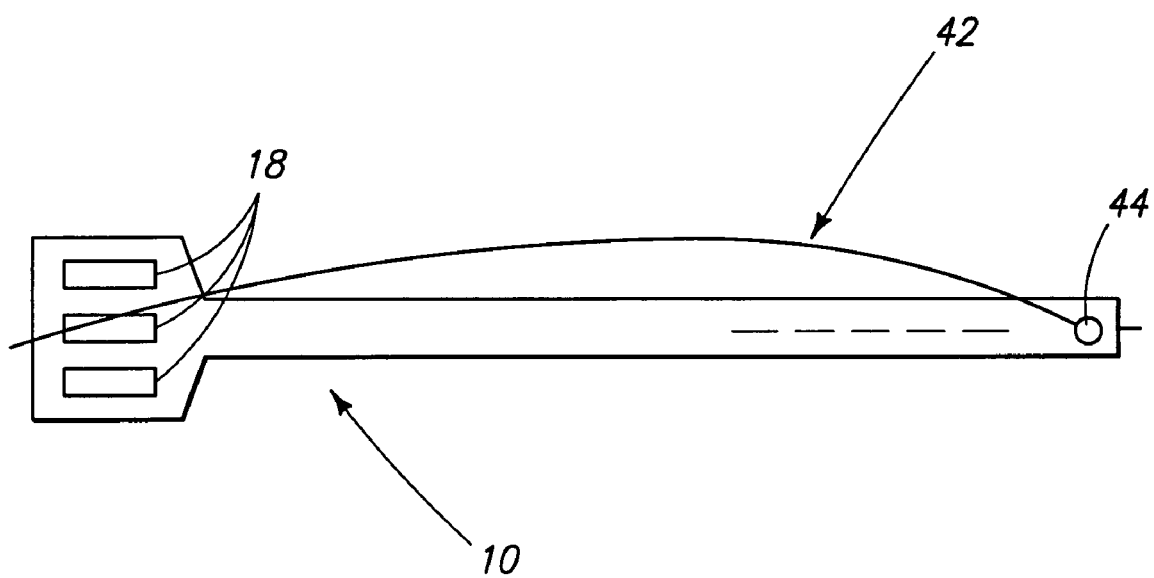
FIG. 4 is a schematic top view of a sensor with a fiber 42 that passes through a hole 44 at the distal end of the fiber and extends to the sensor 10 base.

The fiber 32 can be affixed to, or otherwise provided with, the sensor 10 in any of a variety of ways, as would be appreciated by those skilled in the art. For example, the fiber 32 can be attached to the sensor base 34 so that the fiber 32 can be easily removed together with the sensor 10. FIG. 3A is a schematic side view of a sensor 10 and fiber 32 inserted through the skin with the assistance of a connector 38 and a hollow needle 36 that houses the sensor 10 and fiber 32. FIG. 3B is a schematic side view of the sensor 10 shown in FIG. 3A after removal of the needle 36 via the removable insertion guide 40, leaving the sensor 10 and fiber 32 in place. FIG. 4 shows a schematic top view of a sensor 10 to which a fiber 42 has been affixed by passing the fiber 42 through a hole 44 at the distal end of the sensor 10. Alternatively, the fiber 32 can be affixed to the sensor 10 by inserting the fiber into a groove in the sensor 10, or by using an adhesive or other attachment means sufficient to keep the fiber 32 in close proximity to the sensor 10 upon placement in a biological environment. Affixing the fiber 32 to the distal end of the sensor 10 can facilitate keeping the fiber in position upon placement. Those skilled in the art will appreciate other means by which a fiber can be provided in close proximity to the sensor, without necessarily affixing the fiber directly to the sensor. For example, the fiber can be co-inserted with the sensor at the time of implantation so that the fiber is positioned in close proximity to the sensor.

Therapeutic Agents

A medicinal or therapeutic agent can be incorporated into the hydrophilic material for the coating of the sensor. The agent is selected in accordance with the desired effect. For example, the objective may be to prevent or minimize inflammation or microbial infection. Examples of therapeutic agents include, but are not limited to, anti-inflammatory, anti-bacterial, anti-viral, anti-coagulant, and disinfecting agents, such as dexamethasone, cefazolin, and benzalkonium chloride, and/or a growth factor. In some embodiments, the therapeutic agent may be an anti-proliferative agent that kills growing cells such as microbial organisms or reactive cells. In a preferred embodiment, the hydrophilic coating includes an anti-inflammatory agent, such as dexamethasone or a salt thereof. Suitable water-soluble salts of dexamethasone include, but are not limited to, the sodium phosphate or acetate salts. Dexamethasone serves to reduce inflammation and also to deactivate macrophages, which allows for enhanced sensor performance.

Polymer Layer

In a preferred embodiment, the polymer layer 22 comprises polyurea (see, e.g., U.S. Pat. Nos. 5,777,060 and 5,786,439). Examples of a suitable polymer layer for a biosensor include, but are not limited to, glucose limiting polymer (GLP; Medtronic MiniMed, Inc., Northridge, Calif.). Other formulations of the polymer layer can be selected in accordance with the desired use. For example, U.S. Pat. Nos. 5,777,060 and 5,786,439 describe coatings suitable for use with biosensors, particularly for use with glucose oxidase and glucose detection. These coatings share features in common with GLP, and can be adapted for use with other types of sensors.

Methods

Embodiments of the invention additionally provide a method for producing a biosensor. In one embodiment, the method includes coating a sensor with a hydrophilic polymer. Preferably, the polymer is a PEO-containing polymer that is sprayed or painted onto the sensor as a lacquer. Those skilled in the art will appreciate a variety of manners by which the sensor can be coated and dried. In another embodiment, the method includes affixing a fiber to a sensor or otherwise providing a fiber in close proximity to the external surface of the sensor. The fiber can be affixed to the sensor by attachment to the sensor, preferably at the sensor base and/or to a distal end of the sensor. The fiber can be affixed by adhesion to the sensor and/or by mechanical means, such as by passing the fiber through a hole in the sensor or lodging the fiber into a groove in the sensor. Preferably, the coating or fiber is modified to deliver a therapeutic agent. Embodiments of the invention additionally provide a biosensor produced by the above method.

In addition, embodiments of the invention provide a method for monitoring or detecting a biological substance in a subject. The biological substance may be glucose, lactate, amino acids or other analyte of interest. The method includes contacting a biosensor having an accessory material in accordance with embodiments of the invention with a tissue or biological fluid, such as interstitial fluid or blood, of the subject, and detecting the presence of the substance or analyte via the biosensor. The method provides more efficient and effective substance detection and monitoring because of reduced inflammation and/or biofouling of the biosensor. The method is particularly suited for subjects requiring repeated and/or continuous monitoring of an analyte, such as glucose for people with diabetes.

The invention additionally provides a method of delivering a biologically active substance to a subject comprising implanting a biosensor of the invention into a tissue of the subject, wherein the accessory material comprises the biologically active substance. In a preferred embodiment, the biologically active substance comprises a cytokine, growth factor or therapeutic agent.

The foregoing description of preferred embodiments of the invention has been presented for the purposes of illustration and description. It is not intended to be exhaustive or to limit the invention to a precise form disclosed. Many modifications and variations are possible in light of the above teaching. It is intended that the scope of the invention be limited not by this detailed description, but rather by the claims appended hereto.

What is claimed is:

1. A biosensor comprising an analyte sensor having an external surface, and an accessory material coated with a hydrophilic polymer provided in proximity to the external surface, wherein the accessory material modifies the biological response of a tissue that is in contact with the biosensor, wherein the accessory material is a fiber modified to deliver dexamethasone or a salt thereof.

2. The biosensor of claim 1, wherein the biological response comprises protein deposition, inflammation or proliferation of macrophages or foreign body giant cells.

3. The biosunsor of claim 1, wherein the hydrophilic polymer comprises polyhydroxyethylmethacrylate (PHEMA), polyurethane, polysaccharide, polyacrylamide, or polyurea.

4. The biosensor of claim 1, wherein the hydrophilic polymer comprises polyethylene oxide (PEO).

5. The biosensor of claim 4, wherein the PEO comprises a polyurethane, polyurea or a cross-linked PEO.

6. The biosensor of claim 1, wherein the salt is a sodium phosphate or acetate salt.

7. The biosensor of claim 1, which comprises an enzymatic, molecular recognition, oprochemical or electrochemical sensor.

8. The biosensor of claim 1, which comprises a glucose sensor.

9. The biosensor of claim 1, wherein the fiber comprises cotton, polypropylene, polyurethane, polyester, polylacric acid (PLA), polyglycolic acid (PGA), or a co-polymer of lactic acid and glycolic acid (PLGA).

10. The biosensor of claim 1, further comprising an additional therapeutic agent, which additional agent comprises an anti-inflammatory, anti-bacterial, anti-viral, anti-coagulant, anti-proliferative or disinfecting agent, or a growth factor.

11. The biosensor of claim 1, wherein the fiber is affixed to a distal end of the biosensor.

12. The biosensor of claim 11, wherein the fiber is affixed to the distal end of the biosensor by passage through a hole in the biosensor.

13. The biosensor of claim 1, wherein the fiber is affixed to the biosensor by insertion into a groove in the biosensor.

14. A method of delivering a biologically active substance to a subject comprising implanting a biosensor of claim 1 into a tissue of the subject, wherein the accessory niaterial comprises the biologically active substance.

15. The method of claim 14, wherein the biologically active substance additionally comprises a cytokine, growth factor or therapeutic agent.

16. A biosensor comprising a sensor having an external surface, and an accessory material provided in proximity to the external surface, wherein the accessory material modifies the biological response of a tissue that is in contact with the biosensor, wherein the accessory material is a fiber modified to deliver a therapeutic agent, and wherein the therapeutic agent comprises cefazolin or benzalkonium chloride, wherein the fiber comprises cotton, polypropylene polyurethane, polyesrer, polylactic acid (PLA), polyglycolic acid (PGA), or a co-polymer of lactic acid and glycolic acid (PLGA).

17. The biosensor of claim 16, further comprising an additional therapeutic agent, which additional agent comprises an anti-inflammatory, anti-bacterial, anti-viral, anti-coagulant, anti-proliferative or disinfecting agent, or a growth factor.

18. A biosensor comprising an sensor having an external surface, and an accessory material provided in proximity to the external surface, wherein the accessory material modifies the biological response of a tissue that is in contact with the biosensor, wherein the accessory material is a fiber modified to deliver dexamethasone or a salt thereof, wherein the biosensor comprises an enzymatic, molecular recognition, oprochemical or electrochemical sensor.

19. A biosensor comprising an sensor having an external surface, and an accessory material provided in proximity to the external surface, wherein the accessory material modifies the biological response of a tissue that is in contact with the biosensor, wherein the accessory material is a fiber modified to deliver dexamethasone or a salt thereof, wherein the biosensor comprises a glucose sensor.

20. A biosensor comprising a sensor having an external surface, and an accessory material provided in proximity to the external surface, wherein the accessory material modifies the biological response of a tissue that is in contact with the biosensor, wherein the accessory material is a fiber modified to deliver a therapeutic agent, and wherein the therapeutic agent comprises cefazolin or benzalkonium chloride, the biosensor further comprising an additional therapeutic agent, which additional agent comprises anti-inflammatory, anti-bacterial, anti-viral, anti-coagulant, anti-proliferative or disinfecting agent, or a growth factor.

21. A method of producing a biosensor, comprising:
providing an accessory material in close proximity to the biosensor; modifiying the biological response of a tissue that is in contact with the biosensor using the accessory material,
delivering dexamethasone or a salt thereof, cefazolin or benzalkonium chloride using the accessory material; and coating the fiber with a hydrophilic polymer.

22. The method of claim 21, wherein the biosensor is an analyte sensor.

23. The method of claim 22, wherein the polymer comprises a polyurethane, acrylate, polyester or cross-linked PEO.

24. The method of claim 22, wherein the coating comprises spraying or painting the polymer onto the fiber.

25. The method of claim 21, wherein the fiber is further modified to deliver an additional therapeutic agent.

26. A biosensor produced by the method of claim 21.

* * * * *